United States Patent
Almqvist

(10) Patent No.: US 11,185,650 B2
(45) Date of Patent: Nov. 30, 2021

(54) SELF-CONTAINED BREATHING APPARATUS

(71) Applicant: Hans Almqvist, Southbury, CT (US)

(72) Inventor: Hans Almqvist, Southbury, CT (US)

(73) Assignee: Createc LLC, Branford, CT (US)

(*) Notice: Subject to any disclaimer, the term of this patent is extended or adjusted under 35 U.S.C. 154(b) by 565 days.

(21) Appl. No.: 13/963,059

(22) Filed: Aug. 9, 2013

(65) Prior Publication Data

US 2014/0041662 A1    Feb. 13, 2014

Related U.S. Application Data

(60) Provisional application No. 61/681,234, filed on Aug. 9, 2012.

(51) Int. Cl.
*A61M 16/00*      (2006.01)
*A62B 7/02*       (2006.01)
(Continued)

(52) U.S. Cl.
CPC .... *A61M 16/0045* (2013.01); *A61M 16/0051* (2013.01); *A61M 16/024* (2017.08);
(Continued)

(58) Field of Classification Search
CPC ............ B64D 10/00; B64D 11/00; B64D 2231/00–025; A62B 7/02; A62B 7/00; A62B 7/04; A62B 9/02; A62B 9/022; A62B 9/027; A62B 25/00; A62B 25/005; A62B 7/14; A62B 18/00–10; Y10S 55/35; B63C 11/22; B63C 11/18; B63C 2011/182; A61M 16/0045; A61M 16/0051; A61M 16/06;
(Continued)

(56) References Cited

U.S. PATENT DOCUMENTS 3,710,553 A * 1/1973 Parker .................... A62B 19/00
                                                            128/204.22
4,016,876 A * 4/1977 Martin .................... A62B 7/02
                                                            128/204.23
(Continued)

FOREIGN PATENT DOCUMENTS

EP         0091310 A3    9/1984
GB        2426203 A     11/2006

OTHER PUBLICATIONS

IPRP on Patentability; Lindner, Nora; PCT/US2013/054324; Feb. 10, 2015, Feb. 10, 2015.

(Continued)

*Primary Examiner* — Elliot S Ruddie
(74) *Attorney, Agent, or Firm* — Michaelde Angeli

(57) ABSTRACT

Apparatuses and methods are disclosed for improving the Weight/Duration ratio of Self Contained Breathing Apparatuses (SCBAs) by decreasing the amount of fresh breathing gas required from the system by saving exhaled air that is low in carbon dioxide in a reservoir and reusing it at the subsequent inhalation. Electronic control units ("ECUs") including conventional oxygen sensors and special types of carbon dioxide sensors are used to monitor and predictably regulate the consumption of breathing gas, further contributing to a significantly lower overall system weight for any given duration of the SCBA.

17 Claims, 11 Drawing Sheets

(51) Int. Cl.
   *A61M 16/06* (2006.01)
   *A61M 16/20* (2006.01)
   *A62B 9/02* (2006.01)
   *B63C 11/22* (2006.01)
(52) U.S. Cl.
   CPC ............ *A61M 16/06* (2013.01); *A61M 16/20* (2013.01); *A62B 7/02* (2013.01); *A62B 9/02* (2013.01); *B63C 11/22* (2013.01)
(58) Field of Classification Search
   CPC .. A61M 16/20; A61M 16/201; A61M 16/202; A61M 16/203; A61M 16/204; A61M 16/205; A61M 16/207; A61M 16/208; A61M 16/209; A61M 16/22; A61M 16/009; A61M 16/0093; A61M 16/0891
   USPC ............ 128/204.18, 204.21, 204.22, 204.23, 128/205.13, 205.25, 205.27, 205.28, 128/205.29
   See application file for complete search history.

(56) References Cited

U.S. PATENT DOCUMENTS

| | | | | |
|---|---|---|---|---|
| 4,163,448 | A * | 8/1979 | Grouard | A62B 7/10 128/204.26 |
| 4,567,889 | A * | 2/1986 | Lehmann | A61M 16/00 128/204.28 |
| 4,633,868 | A * | 1/1987 | Itoh | A62B 7/10 128/204.26 |
| 5,036,841 | A * | 8/1991 | Hamilton | A62B 7/10 128/202.26 |
| 6,167,882 | B1 * | 1/2001 | Almqvist | A62B 7/02 128/201.27 |
| 2005/0159844 | A1 * | 7/2005 | Sigafus | F23N 1/002 700/275 |
| 2006/0241508 | A1 * | 10/2006 | Jaffe | A61M 16/0045 600/532 |
| 2006/0260612 | A1 * | 11/2006 | Matthiessen | A62B 7/04 128/205.13 |
| 2011/0297155 | A1 * | 12/2011 | Shelly | A61M 16/00 128/204.23 |

OTHER PUBLICATIONS

International Search Report dated Nov. 25, 2013 in PCT/US2013/054324 (3 pages).
Written Opinion dated Nov. 25, 2013 in PCT/US2013/054324 (6 pages).

* cited by examiner

SELF-CONTAINED BREATHING APPARATUS

CROSS-REFERENCE

This application claims the benefit of priority of presently pending U.S. Provisional Application Ser. No. 61/681,234 filed Aug. 9, 2012 and is incorporated by reference herein in its entirety as if made a part of the present specification.

FIELD OF THE INVENTION

The present invention relates to Self Contained Breathing Apparatuses (SCBA) used by firefighters, other first responders, industrial workers, mine workers, etc. for enabling rescue missions in and escape from contaminated environments. Related equipment includes diving apparatuses (SCUBA) and breathing systems for high altitude flying.

BACKGROUND

Self-Contained Breathing Apparatuses (SCBAs) have a breathing gas containing oxygen, with or without one or more inert gases, stored under pressure in a storage tank and administered to the user through a system of pressure regulators. Generally, there are three types of SCBAs depending on whether or not the exhalation gas is expelled to the ambient environment, or cleaned and reused: 1) Open circuit SCBA with all exhalation gas expelled to the surrounding environment; 2) Closed circuit SCBA using pure oxygen as breathing gas and with all exhalation gas being cleaned from carbon dioxide and reused; and 3) Semi-closed (or semi-open) SCBA with part of the exhalation gas being expelled to the surrounding and the reminder of the gas cleaned of carbon dioxide and reused.

The basics of these systems have been known, and such systems all have their advantages and disadvantages. Based on their different features, the three styles all have specific applications in different market segments. In most applications, the selected systems have to be carried by the users, who often already are overloaded with other types of protective equipment and rescue tools. The Weight/Duration ratio (where "Weight" is the load on the body caused by the SCBA, including the weight of the breathing gas, and where "Duration" is the time the breathing gas lasts under predetermined conditions) is always of utmost interest. However, other considerations are also of importance, such as, for example, physiological factors pertaining to the composition of the breathing gas, the risk of bringing high-concentration oxygen into fires, etc.

Regarding breathing physiology, at medium work load (150 W), a human consumes an average of 40 liters of air per minute, the so called minute volume. The breathing frequency is about 20 breaths per minute, meaning the volume of each breath is about 2 liters. The air flow as function of time is close to a sinus curve with both the inhalation and exhalation phases of approximately equal length, or about 1.5 seconds. The body consumes about 2 liters of oxygen per minute for the metabolism and expels about 1.8 liter of carbon dioxide per minute. The inhalation air contains about 21% oxygen and small amounts of carbon dioxide. The exhalation air contains about 16% oxygen and about 4% carbon dioxide. Of special interest for this patent application is the carbon dioxide percentage in the exhalation air as function of time. See FIG. 1. All numbers are average values for healthy adults and the conditions refer to exercise without wearing a SCBA.

Only a portion of the inhalation air reaches the lungs and takes part in the oxygen/carbon dioxide exchange. Air in the mouth and trachea doesn't take part in the exchange and keeps its original composition. This volume is called the physiological dead air space. When using a SCBA, the dead air space is increased due to cavities in the SCBA's face piece. The dead air space is filled with air from the last part of the exhalation that is high in carbon dioxide at each exhalation and consequently re-inhaled at the next inhalation. That means that the inhalation air always contains a certain amount of carbon dioxide, the larger the dead air space, the higher concentration of carbon dioxide. Carbon dioxide in small quantities (such as, for example, about 2-3%), doesn't present a health risk, but does contribute to increased breathing volume. This, in turn, results in shorter durations for some types of SCBAs. For this reason, official standards normally include maximum values on the re-inhaled carbon dioxide concentration.

About 99% of all firefighters use an open circuit SCBA according to FIG. 2. Open circuit SCBAs have a very unfavorable Weight/Duration ratio. See FIG. 3. In order to reduce carried weight, the selected SCBAs are normally units with rated duration of 30 or 45 minutes. This presents two problems. First, the rating that is performed by a certifying body, CEN, NIOSH or similar, is made at 40 liter per minute ventilation. Especially for shorter durations, the average air consumption for firefighters exceeds the 40 liter per minute ventilation resulting in a reduction in the actual duration, or well under the rated value. As a result, and in spite of their ratings, these SCBAs do not always provide firefighters enough time to perform a meaningful job. Secondly, if the firefighter gets disorientated or trapped, the short duration often doesn't allow adequate reserve time for a rescue operation, leading to numerous injuries and even fatalities.

SUMMARY OF THE INVENTION

One aspect of the present innovation is to offer a SCBA with improved Weight/Duration ratio. This is of special interest to firefighters, who represent the most frequent users of SCBAs. Nearly 3 million SCBAs are used in that market segment worldwide. Contrary to some other user groups (such as, for example, chemical industries where SCBAs are only used at infrequent emergencies), firefighter's SCBAs are in daily use and contribute to saving millions of lives each year, in addition to protecting valuable property, buildings, etc.

According to one aspect, the present disclosure is directed to breathing apparatuses comprising a fresh breathing gas supply, with the supply comprising an oxygen concentration greater than about 21%, at least one supply pressure regulator in gas flow communication with the gas supply, a face piece in gas flow communication with the regulator, a means of directing the breathing gas in predetermined patterns, an exhalation valve, and a flexible volume reservoir (e.g., a breathing bag, etc.), wherein the breathing apparatuses comprises a means for directing an initial portion of an exhalation to the reservoir with the remaining portion of the exhalation being expelled to a surrounding environment, and said breathing apparatus maintains a portion of the exhalation air stored in the reservoir for a subsequent inhalation.

According to a further aspect, the breathing apparatuses comprise a two-way valve for directing exhalation either to the reservoir or to the surrounding environment.

According to a still further aspect, the breathing apparatuses comprise a two-way valve that is maintained in a position open to a reservoir and closed to an exhalation valve, or is maintained in a position open to an exhalation valve and closed to a reservoir.

Still further, according to one aspect of the present disclosure, the position of the two-way valve is controlled by a condition selected from the group consisting of a concentration of carbon dioxide in the exhalation air, a concentration of carbon dioxide in the inhalation air; a concentration of carbon dioxide in a reservoir, a volume of air exhaled into a reservoir, and combinations thereof.

According to a further aspect, the breathing apparatuses further comprise a means to automatically adjust a point between a first setting indicating an "open" position relative to the reservoir and a second position indicating an "open" position to an exhalation valve, and the positioning of the two-way valve is controlled by an electronic control unit.

Still further, according to one aspect, the breathing apparatuses further comprise a reservoir positioned in a breathing gas flow circuit and a carbon dioxide absorber, with the carbon dioxide absorber positioned at a location in the breathing gas flow circuit. The position is selected from the group consisting of: up-stream from the reservoir and down-stream from the reservoir.

In a further aspect, the breathing apparatuses further comprising a reservoir positioned in a breathing gas circuit with no carbon dioxide absorber present in the breathing circuit.

In a still further aspect, the breathing apparatuses further comprise a bypass valve that opens a fresh breathing gas flow into a user's inlet, with the bypass valve in communication with an oxygen sensor for sensing oxygen concentration of inhalation air in the breathing gas flow. According to one aspect, the oxygen sensor sends a signal to a controller when the oxygen concentration of inhalation air in the breathing gas flow is less than a predetermined value.

According to a further aspect, the breathing apparatuses further comprise a bypass valve that opens a fresh breathing gas flow into a user's inlet, with bypass valve in communication with a carbon dioxide sensor for sensing carbon dioxide concentration of inhalation air in the breathing gas flow. According to one embodiment, the carbon dioxide sensor sends a signal to a controller when the carbon dioxide concentration of the inhalation air in the breathing gas flow is greater than a predetermined value.

According to a still further aspect, the breathing apparatuses comprise a means for maintaining breathing gas at positive pressure relative to the ambient pressure, and electronic control unit comprising a pressure sensor, said control unit maintaining the positive pressure of the breathing gas at a predetermined value.

According to a still further aspect, the breathing apparatuses further comprise a start-up check function that automatically tests of predetermined vital functions upon the user's activation and returns a go or no-go response and a means to signal information about the no-go response. According to a preferred embodiment, a signal is sent to a controller in response to a user not breathing. In a further aspect, a signal is sent to a controller in response to a user not breathing.

A still further aspect of the present disclosure is directed to a breathing apparatus comprising a fresh breathing gas supply, said supply comprising an oxygen concentration greater than about 21%, at least one supply pressure regulator in gas flow communication with the gas supply, a face piece in gas flow communication with the regulator, a means of directing the breathing gas in predetermined patterns, an exhalation valve, and a flexible volume reservoir, wherein said breathing apparatus comprises a means for directing an initial portion of an exhalation to the reservoir with the remaining portion of the exhalation being expelled to a surrounding environment. The breathing apparatus maintains a portion of the exhalation air stored in the reservoir for a subsequent inhalation, and an exhalation valve comprising an opening pressure substantially equal to the pressure in the reservoir at a predetermined degree of filling said reservoir.

According to a further aspect, the breathing apparatuses further comprise a two-way valve that is moveable to an open or closed position relative to a reservoir, and further comprise a higher opening pressure for the exhalation valve than a filling pressure of the reservoir.

According to a still further aspect, the breathing apparatuses further comprise an electronic control unit to maintain the two-way valve in an open position relative to the reservoir.

In a further aspect, the position of the two-way valve is controlled by a condition selected from the group consisting of a carbon dioxide concentration present in the reservoir, a carbon dioxide concentration present in inhalation air, a carbon dioxide concentration present in exhalation air, and a volume of air exhaled into the reservoir, and combinations thereof.

According to a further aspect, the breathing apparatuses further comprise a bypass valve that opens a fresh breathing gas flow into a user's inlet, said bypass valve in communication with an oxygen sensor for sensing oxygen concentration of inhalation air in the breathing gas flow. The oxygen sensor sends a signal to a controller when oxygen concentration of inhalation air in the breathing gas flow is less than a predetermined value.

In a still further aspect, the breathing apparatuses further comprise a start-up check function that automatically tests of predetermined vital functions upon the user's activation and returns a go or no-go response, and a means to signal information about the no-go response.

According to a further aspect, the breathing apparatuses comprise a means to convert the breathing gas pattern to an open circuit system.

In a further aspect, a signal is sent to a controller in response to a change in breathing gas pattern and/or in response to a user not breathing.

BRIEF DESCRIPTION OF THE DRAWINGS

Figure 1:
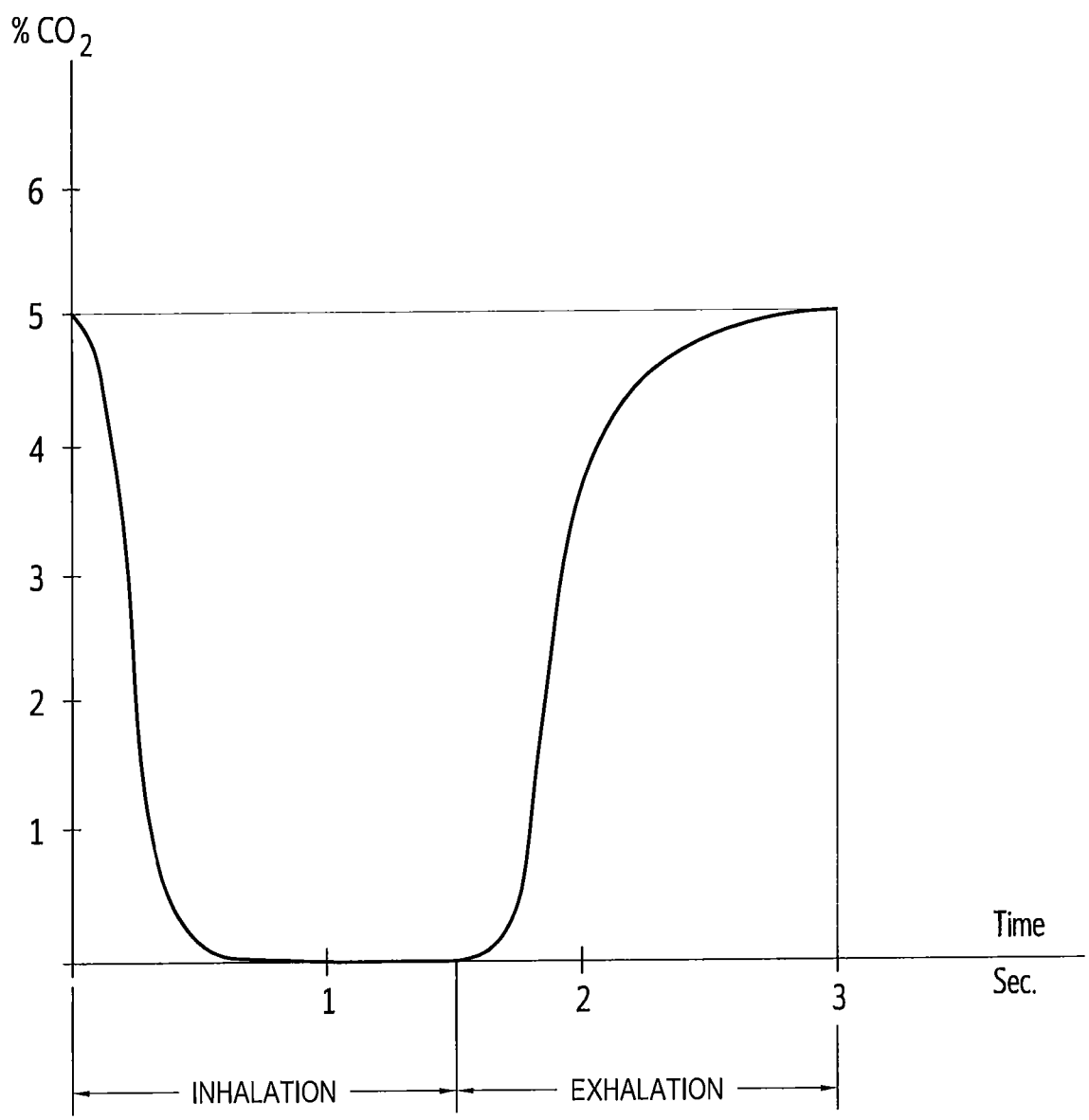
Figure 2:
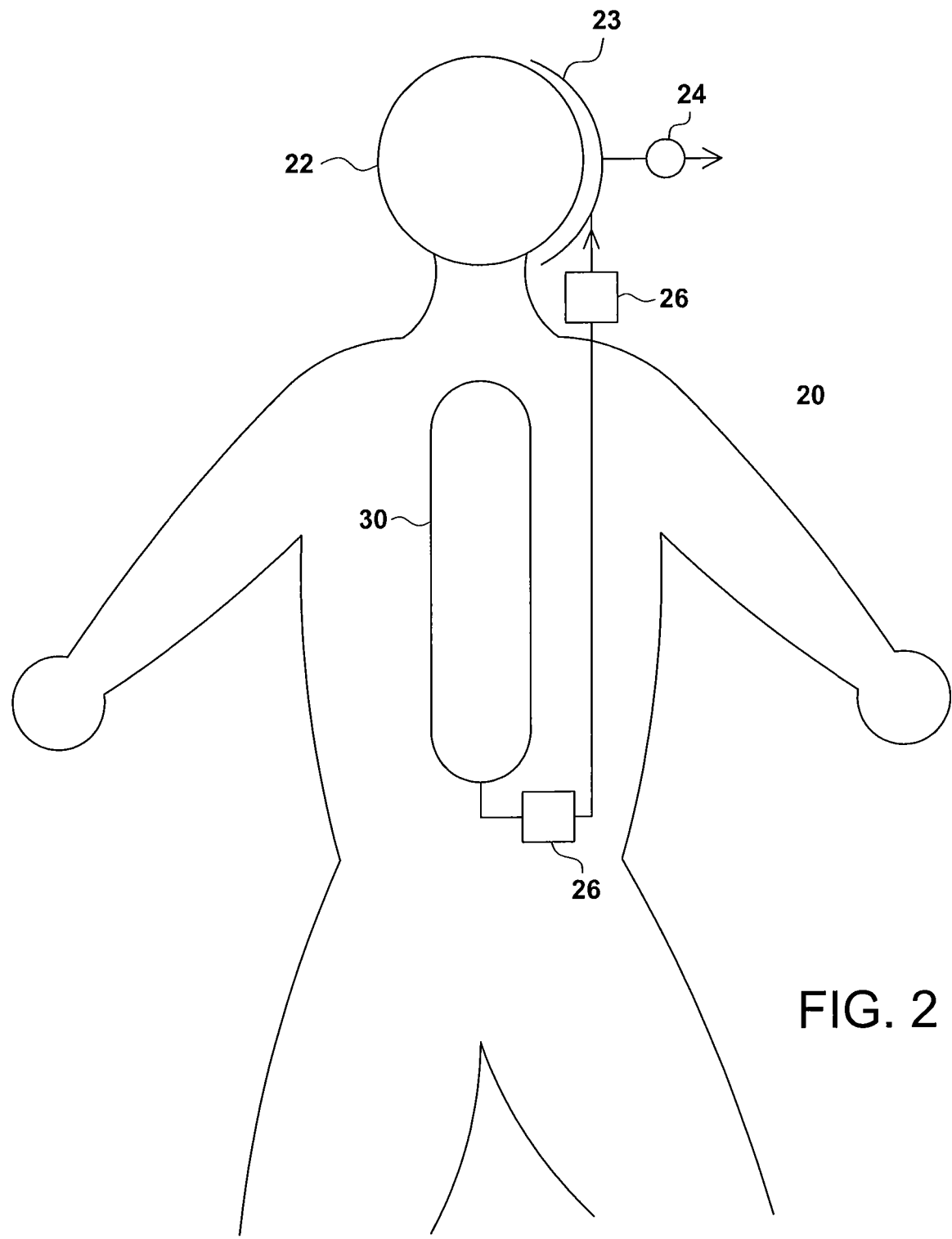
Figure 3:
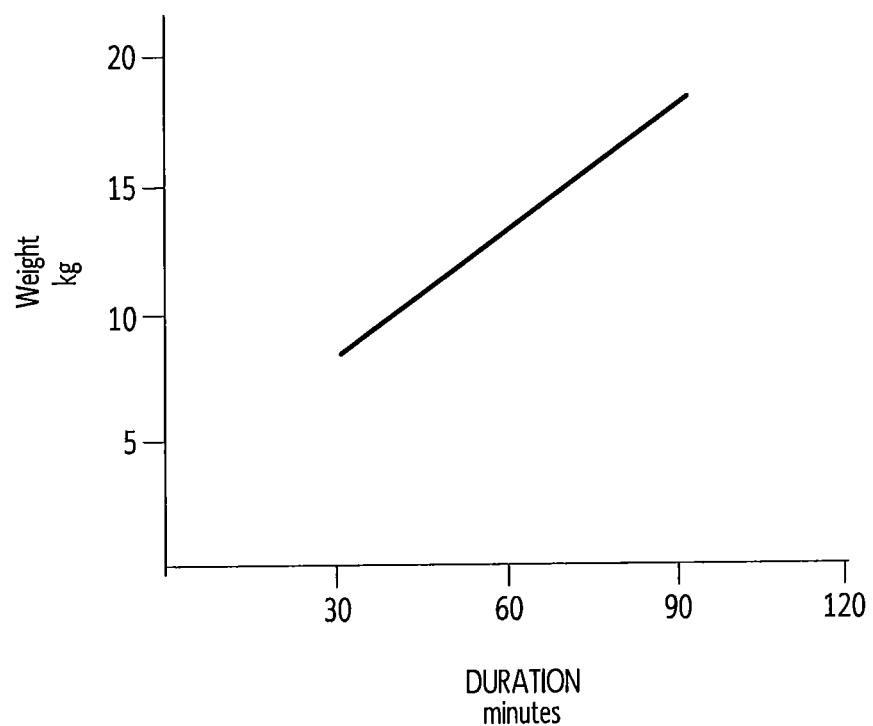
Figure 4:
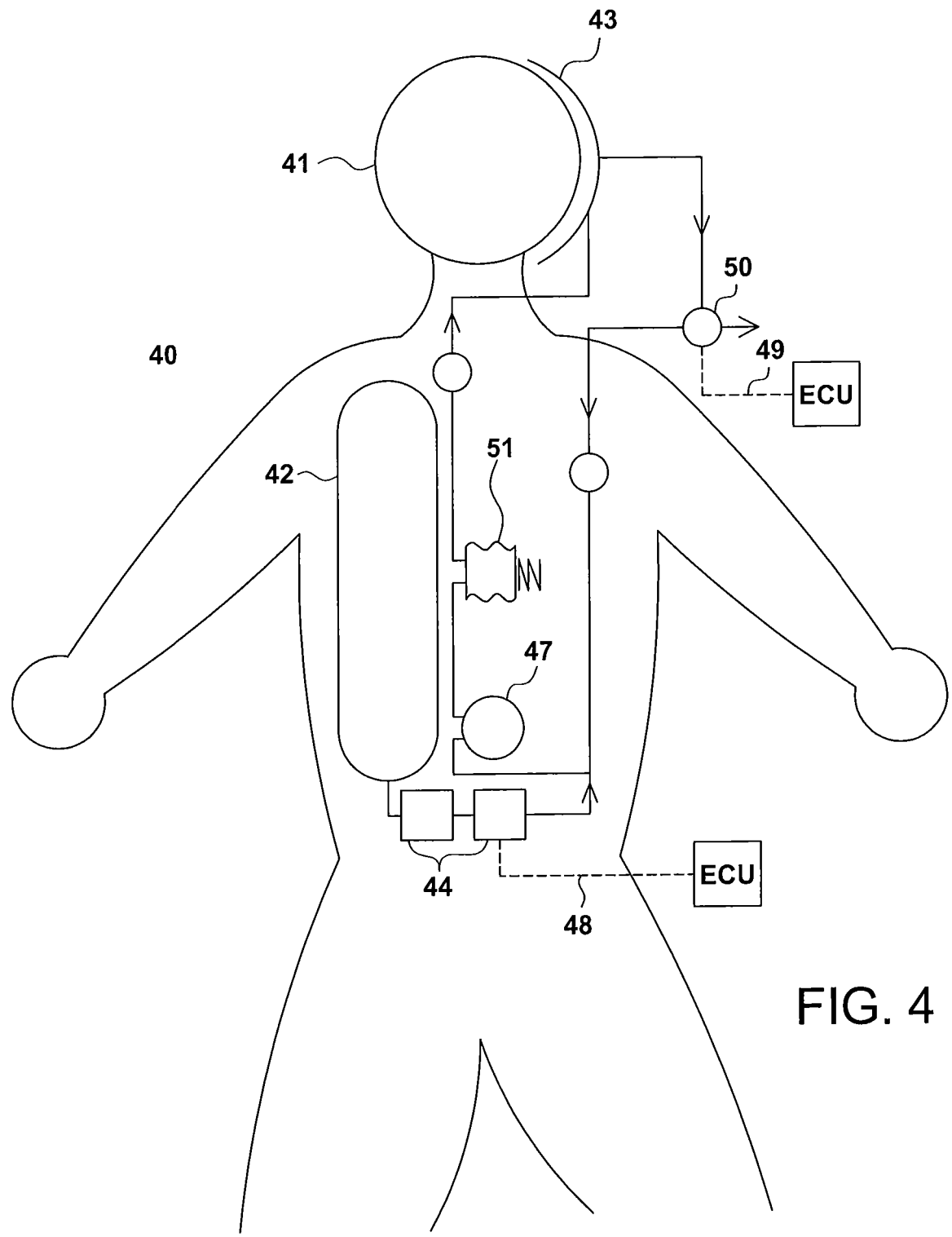
Figure 5:
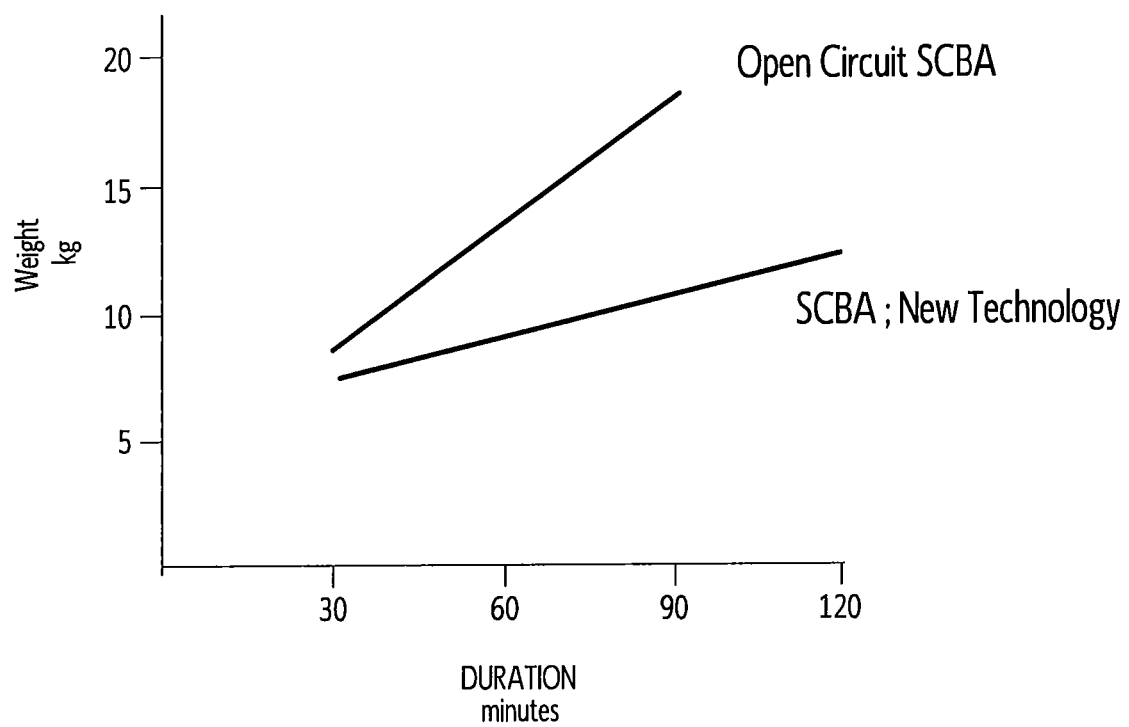
Figure 6:
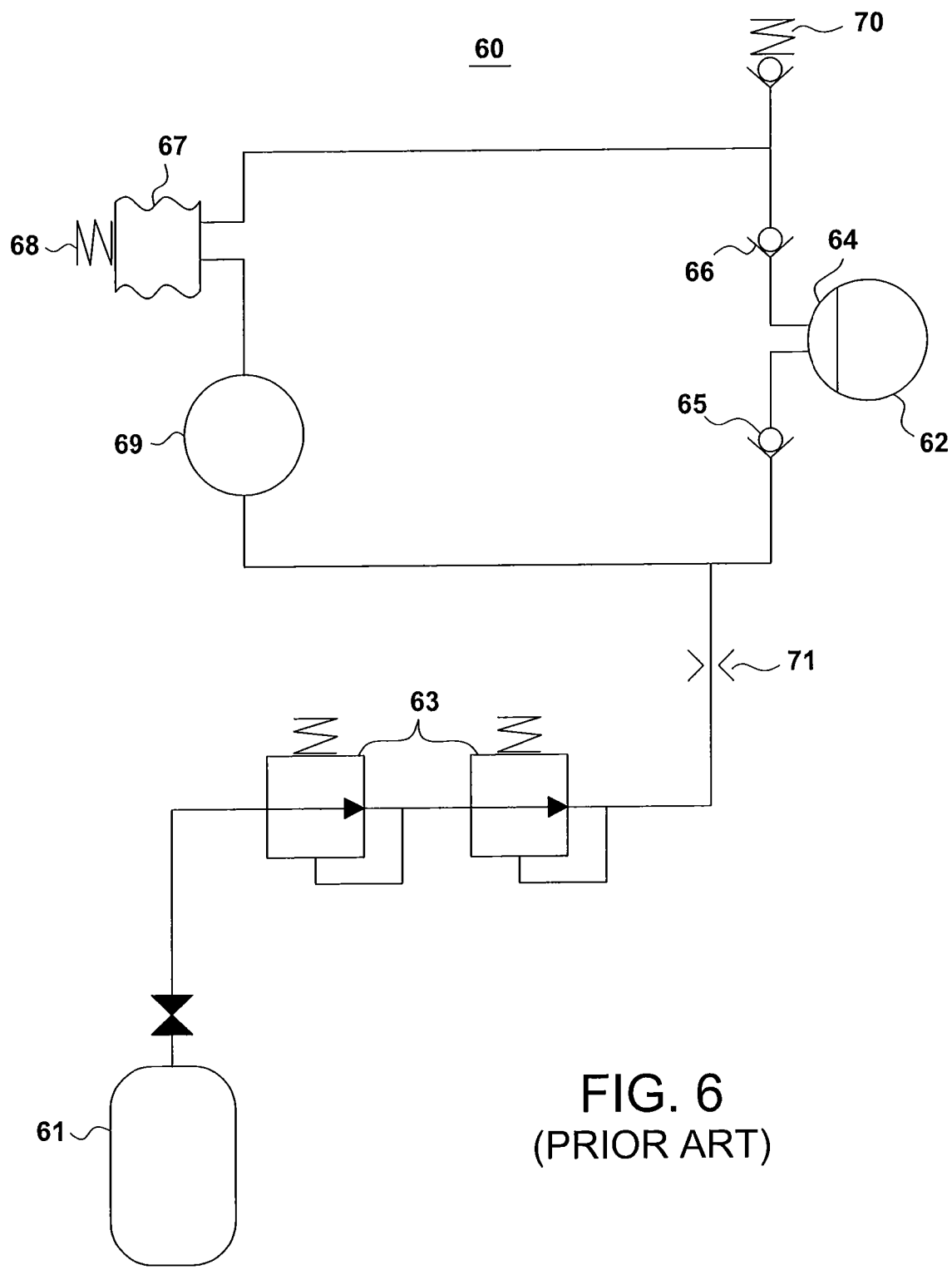
Figure 7:
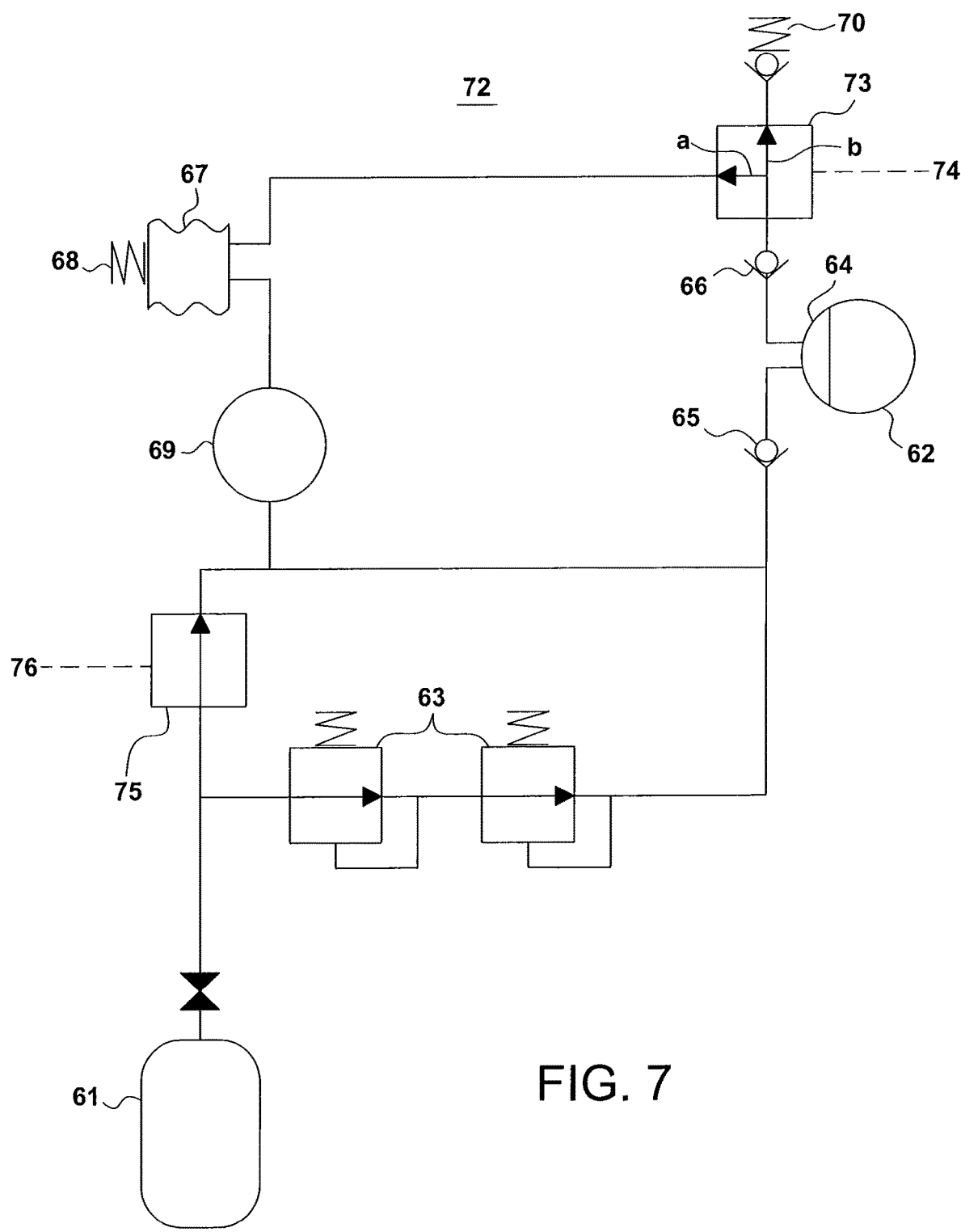
Figure 8:
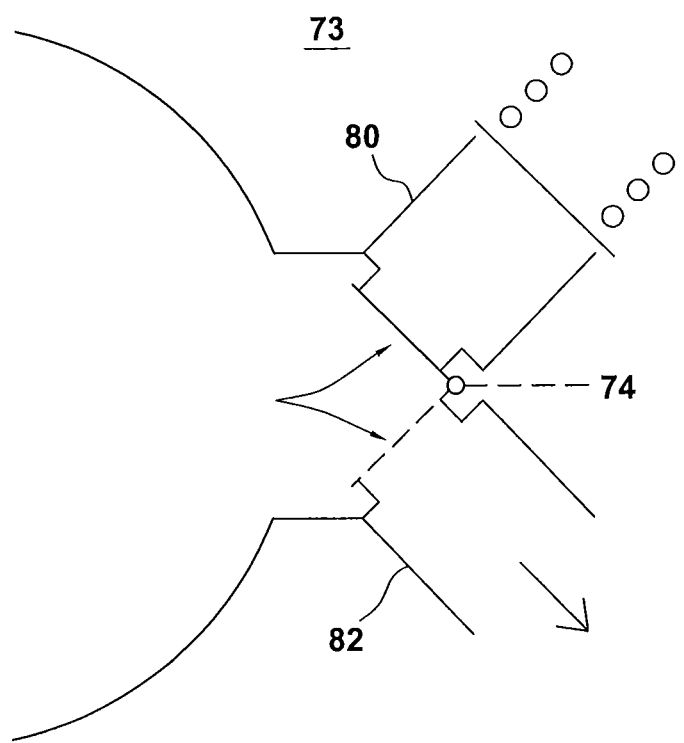
Figure 9:
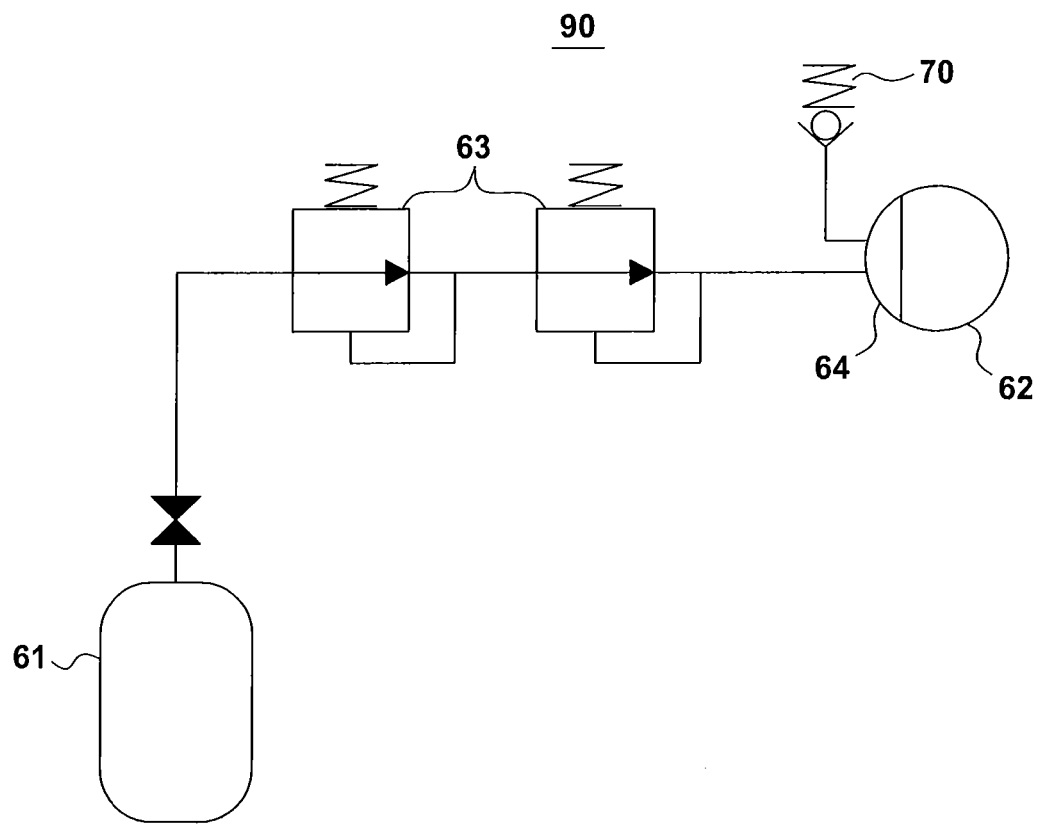
Figure 10:
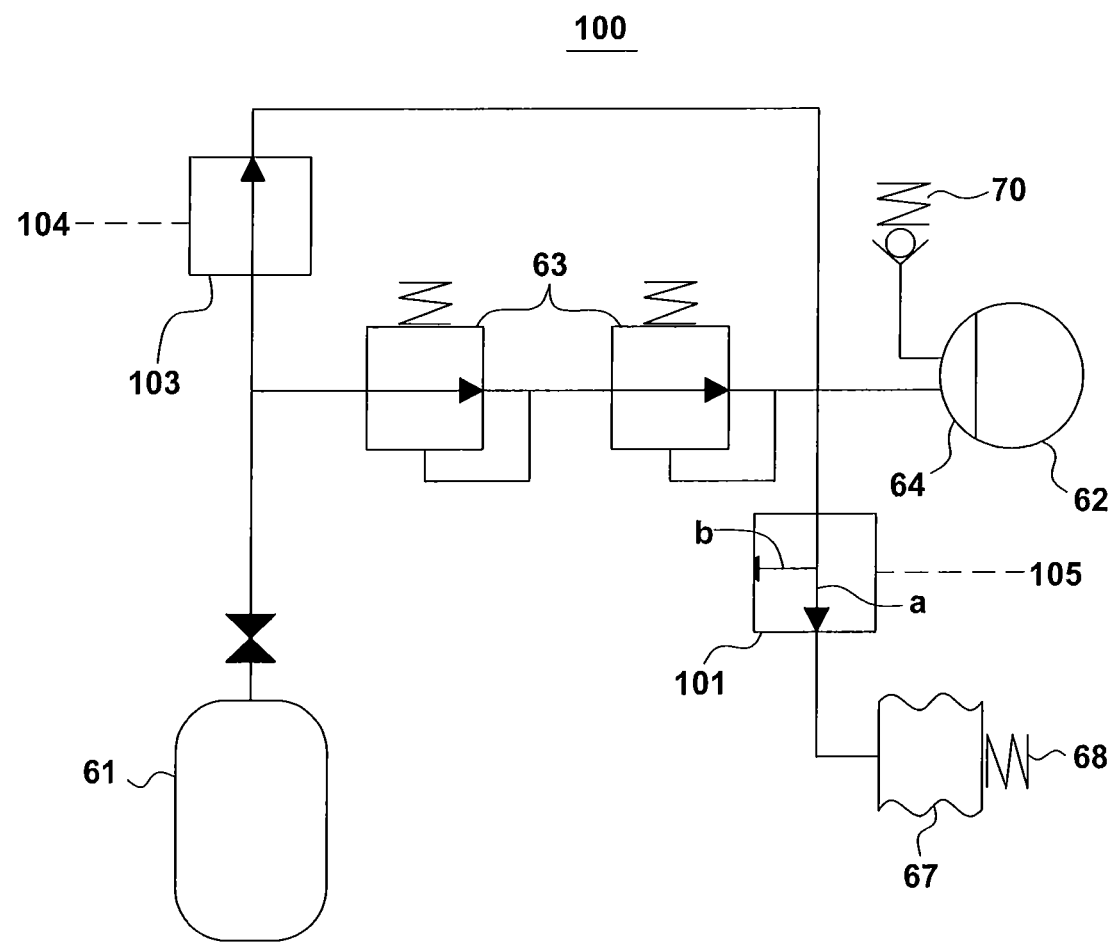
Figure 11:
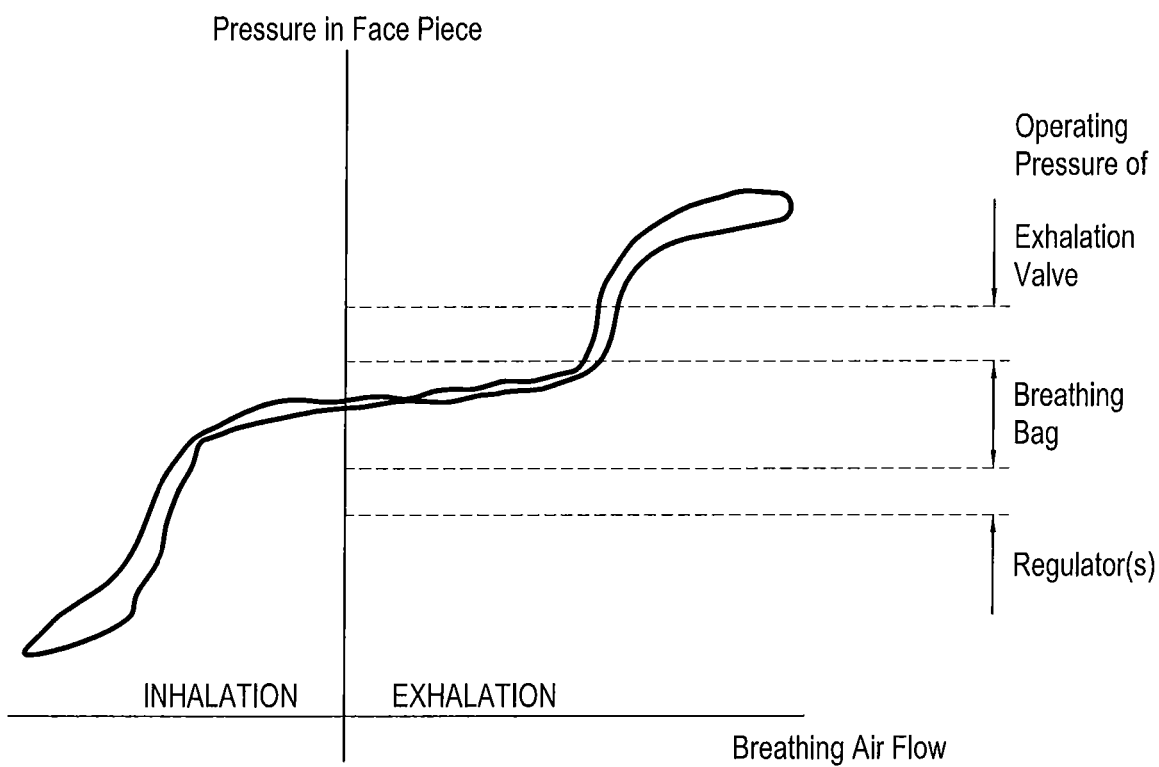

Having thus described variations of the disclosure in general terms, reference will now be made to the accompanying drawings, which are not necessarily drawn to scale, and wherein:

FIG. 1 is a graph depicting the % carbon dioxide as a function of time during inhalation and exhalation cycles;

FIG. 2 is a schematic representation of a known open circuit SCBA system;

FIG. 3 is a graph showing weight/duration ratio for open circuit SCBA systems;

FIG. 4 is a schematic principle overview of one embodiment of the present invention;

FIG. 5 is a graph comparing weigh/duration ratios of known open circuit SCBA with embodiments of the present invention;

FIG. 6 is a schematic representation of a known semi-closed circuit SCBA system;

FIG. 7 is a schematic representation of an embodiment of the present invention;

FIG. 8 is an enlarged view schematic representation of one embodiment of the present invention showing the controlled exhalation airflow from a facemask;

FIG. 9 is a schematic representation of a known open circuit SCBA system;

FIG. 10 is a schematic representation of an alternative of the present invention; and FIG. 11 is a graph showing comparative breathing pressures in a system according to one embodiment of the present invention during inhalation/exhalation cycles.

DETAILED DESCRIPTION

The present invention will be described more fully hereinafter with reference to the accompanying drawings, where preferred alternatives are shown. The disclosures may, however, be embodied in many different forms and should not be construed as limited to the examples set forth. Rather, these examples are provided so that this disclosure will convey the scope of the inventions to those skilled in the field. Like numbers refer to like elements throughout.

One known version of a basic SCBA system (20) is shown in FIG. 2. A user (22) is understood to engage and therefore incorporates a facemask (23), etc. The facemask (23) is in communication with an exhalation valve (24) and regulators (26). The breathing air is supplied via a cylinder under pressure (30), typically with a pressure of about 300 bar.

One of the proposed SCBA designs of the present disclosure is schematically presented in FIG. 4. System (40) comprises a user (41)/face piece (43), in communication with a breathing circuit. As shown, air is supplied from a cylinder (42) through pressure regulators (44). Control assemblies (48) and (49) are shown in the breathing circuit, each preferably comprising a microprocessor, or electronic control unit (ECU) for monitoring pressure and oxygen concentration (48) and the amount of expelled air based on, for example, carbon dioxide concentration (49). Exhalation valve (50) is shown attached to and controlled by control assembly (49). The breathing air is directed in the breathing circuit to carbon dioxide absorber (47) and breathing bag (51). In principle, system (40) comprises a semi-closed system. The breathing gas used and provided from cylinder (42) is preferably air with an increased oxygen concentration, up to 30% oxygen at a contained pressure of about 300 bar. This oxygen concentration limit is equal to what is accepted by authorities from the standpoint of fire risk dependent on elevated oxygen concentration. By using the oxygen-rich air, each amount of air can be used for two to three breaths before the oxygen concentration reaches the 16% level (when it is no longer usable in the lungs for oxygen/carbon dioxide exchange).

Known semi-closed and closed SCBAs use a breathing bag for preserving the exhalation gas for the next breath, and a carbon dioxide absorber for cleaning the exhalation air from carbon dioxide. The systems of the present disclosure are no exception to that pattern. However, according to one aspect the present disclosure, electronic control units ("ECUs") in FIG. 4 referred to as control assemblies 48 and 49, preferably comprise microprocessors that are used to monitor and predictably regulate the consumption of air, thereby minimizing the size of these components and contributing to a significantly lower overall system weight.

FIG. 5 shows a graph comparing one embodiment of the present invention to the known open circuit technology (as determined herein below). The graph indicates that embodiments of the present disclosure make it possible to offer a 60 minute SCBA with a weight equal to that of a presently-known 30 minute unit. The double capacity achieved according to embodiments of the present disclosure significantly contributes to saving many lives while increasing the efficiency of the firefighter operation.

Aspects of the present disclosure include a regulator system that keeps the pressure in the breathing system at a slight over-pressure in order to avoid in-leakage of contaminated atmosphere from the surrounding environment. Preferred embodiments also include a monitor for said positive pressure as well as warning systems for low container pressure, low oxygen level and high carbon dioxide level.

Further aspects of the present disclosure include at least two major changes compared to the known systems; namely: 1) improvements in the breathing bag; and 2) improvements in the carbon dioxide absorber.

Breathing Bag

Presently known semi-closed SCBAs typically have breathing bags with a volume of about 5 liters. This is required by certifying authorities since the user's breathing volume varies during a rescue operation and the bag should always be able to deliver a full breath in order to save the gas in the gas container. This is especially important for closed circuit SCBAs, which have a very small oxygen container. According to aspects of the present disclosure, there is considerably more breathing air in the container that can be used to meet the user's demand, without significantly impacting the duration of the unit. Aspects of the present disclosure further contemplate reducing the breathing bag to about 2 liters or less, consequently saving additional space and weight.

Carbon Dioxide Absorber

As explained above, the air in the so-called dead air space doesn't participate in the oxygen/carbon dioxide exchange in the lungs, and has a comparatively low carbon dioxide concentration. That amount of air in the dead space is the first air to be exhaled during the exhalation phase. See FIG. 1. If such air is saved in the breathing bag, it can be used for re-inhalation with little or no removal of carbon dioxide. The last amount of the exhalation air contains high amounts of carbon dioxide and shall be expelled in order to avoid the need for carbon dioxide removal.

Aspects of the present disclosure comprise the means to save as much exhalation air with low carbon dioxide concentration as possible for the next inhalation, while expelling the exhalation air having high carbon dioxide concentration. In this way, the carbon dioxide absorber can be reduced in size considerably, or even eliminated.

Both features lead to improvements in weight and space compared to known technologies and designs. Selecting the feature to use is dependent on the regulatory authority's eventual decision-making regarding the allowable levels of carbon dioxide in the inhalation air.

As mentioned above, increased carbon dioxide in inhalation air leads to increased ventilation. For an open circuit SCBA, this results in lower duration. For that reason, the level of average carbon dioxide in the inhalation air is set to the order of about 1% (based on the dead air space in the face piece only and measured at certain ventilation). According to further aspects of the present disclosure, in a sensor controlled system, the breathing gas consumption is controlled by the carbon dioxide production that is dependent on the work load only. The allowable average carbon dioxide concentration in the inhalation air can therefore be set relatively high; such as, for example, up to about 2% without any significant negative effect to the user.

As background to describing one aspect of the present disclosure, the typical function of semi-closed SCBAs is presented. See FIG. 6. Breathing gas with elevated oxygen concentration is stored in a container (61) at a pressure of, for example, about 300 bar. Breathing gas is supplied to the SCBA user (62) via one or more pressure regulator(s) (63). The basic supply of fresh breathing gas is arranged as a constant flow via an orifice (71) that is set to give the user enough oxygen for his average work load. Furthermore there are functions (not shown) for supply of extra breathing gas if the pressure in the breathing circuit falls under a predetermined pressure and, optionally, if the oxygen concentration in the inhalation gas is too low. The user (62) is connected to the breathing circuit via a facemask, nose cup or mouth piece, collectively designated "face piece" (64). The breathing gas is directed into the breathing circuit via the non-return valves (65) and (66). A breathing bag (67) is filled during the exhalation. With the help of a spring or similar means (68), a slight overpressure is created in the entire breathing circuit. Upon inhalation, breathing gas from the breathing bag passes a carbon dioxide absorber (69) where the carbon dioxide content is removed, is mixed with fresh air from the container (61), and continues to the user via the inhalation valve (65). An overpressure valve (70) (later referred to as an "exhalation valve") expels excess air and ensures that the pressure in the breathing circuit stays within limits compliant with acceptable physiological values for human breathing. For purposes of this application, the terms "reservoir" and "breathing bag" are equivalent.

In known configurations, the described system has the potential to give the same or slightly better Weight/Duration ratios compared to open circuit SCBAs (see FIG. 3) in spite of the extra weight for the breathing bag (67) and carbon dioxide absorber (69) for durations under one hour and produces better Weight/Duration ratios as compared to open circuit SCBAs for durations over one hour. Therefore, in known configurations, the system may have applications for longer durations, but are not presently considered for firefighter use for durations under one hour; especially as they have the disadvantage of requiring more maintenance than open circuit SCBAs, and deliver a breathing gas that has increased temperature and humidity (because the carbon dioxide absorption is an exothermic process that produces heat and water).

Embodiments of the present innovation significantly minimize mentioned disadvantages of known systems, and offer a potential Weight/Duration ratio as shown in FIG. 5. The diagram is based on the following calculation for a 60 minute rated SCBA (All weights in kg):

| SCBA Model | SCBA Components (kg) | Breathing Gas (kg) | Breathing Gas Container (kg) | Total (kg) |
|---|---|---|---|---|
| Open Circuit SCBA | 5.2[1] | 3.1 | 5.2 | 13.5 |
| Designs According to the Present Disclosure | 6.0[2] | 1.0 | 2.2 | 9.2 |

[1]Carrying Device, Face Mask, Two Pressure Regulators, Pressure Gauge with Hose, Low Air Warning Device, Cylinder Valve, Battery, and Electronics.
[2]Carrying Device, Face Mask, Pressure Regulator, Pressure Gauge with Hose, Low Air Warning Device, Two liter Breathing Bag, Small or No $CO_2$ Absorber, Cylinder Valve, Battery, and Electronics.

FIG. 7 shows a basic design of one embodiment of the present disclosure (72). Most components of this embodiment are found in the prior art system shown in FIG. 6 and the reference numbers (61) through (70) refer to the same components. However, there are many significant differences shown in the embodiments of the present disclosure. For example, the oxygen concentration of the breathing gas in the container (61) is pre-selected between from about 25 to about 30% to: 1) be large enough to support two breaths or more; and 2) to come under the current (2012) maximum concentration allowed for breathing apparatus used in fires. Further, pressure regulator(s) (63) deliver breathing air to the breathing circuit when the pressure in the breathing circuit reaches a predetermined value; a so-called "demand system". In addition, the breathing bag (67) can be made much smaller than presently known systems. For prior art systems, official standards require a breathing bag having a capacity of 5 liters. According to embodiments of the present invention, new designs having a demand system are free from that requirement. As a result, the breathing bag need only have a capacity of two liters or less, resulting in lower weight and, as explained in detail below, aspects of the present disclosure deliver less carbon dioxide into the breathing circuit. This allows the carbon dioxide absorber of the present disclosure to be made smaller and lighter (or eliminated), with less heat and less water produced in the absorber.

One important feature according to embodiments of the present invention is the presence of a valve (73) that has two distinct positions: "a", (open to the breathing bag (67)), or "b" (open to the exhalation valve (70)). For the beginning of each exhalation, the valve is in the "a" position. When carbon dioxide content reaches a pre-determined percentage, (see FIG. 1), the valve switches to the "b" position. See "a" and "b" in FIG. 7. One basic control function (74) for the valve is a carbon dioxide sensor of special type described below for measuring the carbon dioxide percentage in the exhalation breath. According to one embodiment, an integrated electronic control unit controls the valve. One advantage, according to embodiments of the present invention, is a significant reduction in the amount of carbon dioxide delivered into the breathing circuit, along with the advantages described above.

The two-way valve can take a number of different forms. FIG. 8 shows one example for a preferred design for a two-way valve (73). Control unit 74 controls the flow of air in the breathing air/gas circuit such that exhaled air (shown by arrows) is either directed through exhalation portion of the valve (80), or directed to the breathing bag through valve portion (82). As mentioned above, the most direct control function for the two-way valve (73) is the carbon dioxide content in the exhalation air. Because a number of functions in the User/SCBA system are interrelated, other control functions can be selected to control the position of the valve via a controller. Some examples include, for example, carbon dioxide concentration in the inhalation air; carbon dioxide concentration in the breathing bag; time from the start of the exhalation; volume exhaled into the breathing bag, etc.

Due to the many variables in the use of a SCBA, such as, for example, work load, user's experience and health, temporary dislodging of the face piece, etc., the system can be influenced to give incorrect breathing gas composition. For that reason, the system as shown in FIG. 7, has a bypass valve (75) that is set to deliver fresh breathing gas to the breathing circuit at high carbon dioxide and low oxygen concentration via control function (76). The corresponding sensors in control function (76) operate independently from the carbon dioxide used for controlling valve (73), and work with an electronic control unit to control a simple on-off valve in the supply system, and by-passing the pressure regulator(s) (63). The activation of valve (75) is preferably equipped with a warning feature (not shown) that signals the user of its activation.

A contemplated alternative design of the present disclosure has a similar concept as the basic design presented above. Instead of basing this system design on a semi-closed SCBA, it is based on a known open circuit SCBA (see FIG. 9). In this system (90), breathing gas, normally atmospheric air with an oxygen content of about 21% and a nitrogen content of about 79%, is stored in a container (61) under a pressure of, for example, about 300 bar. The breathing gas is supplied to the user (62) via one or more regulator(s) (63), and a face piece, nose cup, or mouth piece, collectively designated face piece, (64), normally under a slight overpressure to avoid in leakage of ambient air. The supply is created on demand, such that, when the user is inhaling and the pressure has reached a certain value, the regulator(s) are opening and supplying an inhalation breath. When the exhalation phase starts, the regulator(s) are closed and the air is directed to an exhalation valve (70) and expelled to the surrounding environment.

FIG. 10 shows the basic design of another aspect of the present disclosure. The components are similar to some components in the previously described systems, and the reference numbers are the same. However this system has the following significant improvements and differences. For example, the oxygen concentration of breathing gas in container (61) is selected to between from about 25 to about 30% to: 1) be large enough to support two breaths or more; and 2) to comport with current (2012) maximum concentration allowed for breathing apparatuses used in connection with firefighting. In addition, the system has a breathing bag (67), loaded with a spring or equivalent means (68) to create and control overpressure in the bag. The breathing bag has a predetermined maximum volume selected in relation to the average volume of the user's breaths. As one example, the breathing bag has a maximum volume of one liter. Still further, the filling pressure for the breathing bag is set to values over the pressure created by regulator(s) (63) and under the opening pressure of the exhalation valve (70). See FIG. 11 showing a Pressure/Flow diagram for one breath.

One principle object in embodiments of the present invention is the presence of a valve (101) that has two distinct positions: "a" (open to the breathing bag (67)), or "b" (closed to the breathing bag (67)). See "a" and "b" in FIG. 10. With the help of a control function, described below, the valve (101) is in the open position (the "a" position) most of the time. Upon inhalation, the user (62) gets the first part of the breath from the breathing bag (67), having larger pressure than the opening pressure of the regulator(s) (63). When the bag is empty, the regulator(s) (63)will deliver the rest of the breath. Upon exhalation, the first part of the breath with low carbon dioxide content (see FIG. 1) will fill the breathing bag (67), as the opening pressure is lower than the opening pressure for the exhalation valve (70). When the breathing bag (67) is full, the pressure increases and the exhalation valve (70) opens, and air with high content of carbon dioxide is expelled to the surrounding environment.

As shown in FIG. 10, the control function of the valve (101) consists of a carbon dioxide sensor (not shown), described below, that measures the carbon dioxide percentage in breathing bag (67). When the carbon dioxide level reaches a predetermined value, such as, for example about 3%, the valve (101) is moved to the "b" position via control function (105) and stays in that position for a predetermined time, such as, for example about 10 seconds. During that time, the system is converted to an open circuit system to protect the user from excessive carbon dioxide concentrations in the inhalation air that can occur at rest, or other situations when the user has very small breath volumes, and all or most of the exhalation would be re-inhaled.

Due to the interrelationship between different functions in the User/SCBA systems of the present disclosure, other control functions and/or monitored conditions can be selected to change the position of valve (101), including, for example, carbon dioxide concentration in the inhalation air; carbon concentration in the exhalation air; and volume exhaled into the breathing bag, etc.

Due to the many variables in the use of the presently disclosed SCBA designs (including, for example, work load, user's experience and health, temporary dislodging of the face piece, mistakes in the composition of the gas in the breathing gas container, etc.), the oxygen content of the inhalation gas could fall below about 21%. For at least this reason, the presently disclosed systems preferably have an oxygen sensor measuring the oxygen concentration in the inhalation air, and a means to administer a constant flow of breathing gas directly into the supply line and to the face piece via a bypass valve 103, and controlled by control functions 104. See FIG. 10. The activation of valve (103) is preferably equipped with a warning feature (not shown) that signals the user of its activation.

A further design contemplated by aspects of the present disclosure provides a breathing bag (67) function by having a face piece (64) with flexible volume. FIG. 10 shows that the valve (101) and breathing bag (67) are in fluid contact with the face piece (64). Therefore, it is also possible for persons experienced in the field to integrate the breathing bag function into the face piece (64). One objective of such alternative designs is to present a simple, low cost, and reliable conversion (such as, for example, a retrofit, etc.) of presently known open circuit SCBAs in order to significantly increase (i.e. double) their duration for a given weight. In addition, the system could be modified, such as, for example, by having a variable breathing bag volume that would be altered relative to a user's air per minute volume.

The preferred carbon dioxide sensor technology required to facilitate an accurate control of the breathing gas composition would be small, inexpensive, reliable, and have a response time of about 20 milliseconds or less. Such technology is available and presently used in other life-saving devices. See, for example, U.S. Pat. No. 7,500,483. Suitable sensors can be obtained from SenseAir AB, Delsbo, Sweden.

The preferred oxygen sensor technology needed to ensure an oxygen concentration of 21% or higher in the inhalation breathing gas requires a response time of about 1 second and is presently available. Such technologies are presently available, such as, for example from Teledyne and MaxTex, etc.

Because a failure of a SCBA would pose an immediate threat to the user's life, preferred designs according to the present disclosure include a number of safety features. Examples of such safety features include, for example, a start-up check to control the proper function of valves, electronics, etc. This function contemplates an automatic run-through of a number of tests, such as, for example, breathing gas content tests, oxygen concentration tests, flow rate tests, positive mask pressure tests, breathing gas concentration tests, electronic control unit function tests, etc. The automatic run-through would preferably take place immediately upon activation by the user and would preferably give the user a visible and/or audible indication that every function has passed its tests. The user would also preferably by given specific visible and/or audible indication of the location of any defect in case of a failed start-up check. Other safety features include, a fail-safe electronic control unit that would react to any electronic failure by automatically setting the breathing circuit to an open circuit mode and give warning both to the user and remotely, such as, for example, to a control center and/or the incident commander, etc. Further contemplated safety features include an immediate signal remotely, such as, for example to a command center as well as an incident commander, in the event that the user's breathing stops.

The present disclosure further contemplates improvements to the efficiency of the system such as influencing the trigger point between saving and dumping the expiration gas by allowing individual breathing patterns and/or one or more previous breaths towards saving more breathing gas.

According to the present disclosure, the system could also be modified to reduce the weight of the SCBA equipment by replacing the mechanical regulator(s) that appear in FIG. 7 and FIG. 10 with a valve controlled by an electronic control unit that would include a pressure sensor that, for example, controls the pressure in the breathing circuit at a predetermined value.

While the preferred variations and alternatives of the present disclosure have been illustrated and described, it will be appreciated that various changes and substitutions can be made therein without departing from the spirit and scope of the disclosure. Accordingly, the scope of the disclosure should only be limited by the accompanying claims and equivalents thereof.

I claim:

1. A breathing apparatus for firefighters and other workers who must work in noxious environments, said breathing apparatus providing partial re-use of exhaled gas for rebreathing, and comprising:
    a fresh breathing gas supply, said breathing gas comprising an oxygen concentration elevated with respect to atmospheric air and of between greater than 21% and 30% oxygen;
    at least one supply pressure regulator in gas flow communication with the breathing gas supply;
    a face piece in gas flow communication with said at least one supply pressure regulator;
    an exhalation valve in gas flow communication with the face piece
    a flexible volume reservoir of no more than 2 liters capacity in gas flow communication with the face piece;
    an electronic control unit;
    a sensor for measuring a concentration of $CO_2$ in the exhaled breathing gas, with a response time of on the order of 20 milliseconds or less, said sensor providing a signal indicative of the concentration of $CO_2$ in the exhaled breathing gas to said electronic control unit; and
    a controllable valve in gas flow communication with the face piece responsive to said electronic control unit, and operable to direct an initial portion of an exhalation to the reservoir for inhalation upon the next inhalation, and, when the $CO_2$ content of the exhalation as measured by said sensor reaches a predetermined value, to direct a subsequent portion of the exhalation to a surrounding environment, via the exhalation valve;
    wherein said at least one supply pressure regulator is operated to maintain the pressure in said face piece at greater than ambient pressure and said flexible volume reservoir is biased to allow maintenance of the pressure in said face piece at greater than ambient pressure; and
    wherein the volume of exhaled breathing gas collected in the reservoir varies with the quantity of gas exhaled, and wherein the reservoir is emptied such that a pressure in the reservoir is equal to an opening pressure of the at least one regulator, and
    whereby the breathing apparatus allows efficient employment of breathing gas by collecting a carbon dioxide-poor and oxygen-rich initial portion of each exhalation in said reservoir for rebreathing, and also provides overpressurization of the face piece to prevent entry of ambient atmosphere.

2. The breathing apparatus according to claim 1, wherein said exhalation valve opens at an opening pressure substantially equal to the pressure in the reservoir at a predetermined degree of filling said reservoir.

3. The breathing apparatus according to claim 2, wherein the breathing apparatus is converted to an open circuit system in response to the carbon dioxide concentration in the breathing air exceeding a predetermined value.

4. The breathing apparatus according to claim 3, wherein a signal is sent to a controller wherein the breathing apparatus is converted to an open circuit system.

5. The breathing apparatus according to claim 1, wherein the controllable valve is a two-way valve, and wherein said two-way valve is normally maintained in a position open to the reservoir and closed to the exhalation valve.

6. The breathing apparatus according to claim 1, wherein the controllable valve is a two-way valve, and wherein said two-way valve is normally maintained in a position open to the exhalation valve and closed to the reservoir.

7. The breathing apparatus according to claim 1, wherein the reservoir is positioned in a breathing gas flow circuit with a carbon dioxide absorber.

8. The breathing apparatus according to claim 1, wherein said controllable valve is a two-way valve that is moveable to an open or closed position relative to the reservoir.

9. The breathing apparatus according to claim 8, wherein said electronic control unit maintains the two-way valve in an open position relative to the reservoir.

10. The breathing apparatus according to claim 1, further comprising a bypass valve that opens a fresh breathing gas flow into the face piece, said bypass valve being in communication with an oxygen sensor for sensing oxygen concentration of inhalation air in the breathing gas flow.

11. The breathing apparatus according to claim 10, wherein the oxygen sensor sends a signal to a controller when the oxygen concentration of inhalation air in the breathing gas flow is less than a predetermined value.

12. The breathing apparatus according to claim 1, further comprising a controller implementing a start-up check function that automatically tests for predetermined vital functions upon the user's activation and returns a go or no-go response.

13. The breathing apparatus according to claim 12, further comprising an indicator to signal information about the no-go response.

14. The breathing apparatus according to claim 1, wherein a signal is sent to a controller in response to a user not breathing.

15. The breathing apparatus according to claim 1, further comprising an electronic control unit comprising a pressure sensor, said control unit controlling said supply pressure regulator so as to maintain the positive pressure of the breathing gas at a predetermined value.

16. The breathing apparatus according to claim 1, further comprising a bypass valve that opens a fresh breathing gas flow into the face piece, said bypass valve being in communication with a carbon dioxide sensor for sensing carbon dioxide concentration of inhalation air in the breathing gas flow.

17. The breathing apparatus according to claim 16, wherein the carbon dioxide sensor sends a signal to a controller when the carbon dioxide concentration of inhalation air in the breathing gas flow is greater than a predetermined value.

* * * * *